(12) United States Patent
White et al.

(10) Patent No.: US 10,493,017 B2
(45) Date of Patent: Dec. 3, 2019

(54) COMPOSITIONS FOR PROVIDING FRIZZ-FREE WAVY HAIRSTYLES USING LOW HEAT

(71) Applicant: Kao USA Inc., Cincinnati, OH (US)

(72) Inventors: Angela M. White, Cincinnati, OH (US); Sean Steigerwald, Cincinnati, OH (US)

(73) Assignee: Kao USA Inc., Cincinnati, OH (US)

( * ) Notice: Subject to any disclaimer, the term of this patent is extended or adjusted under 35 U.S.C. 154(b) by 347 days.

(21) Appl. No.: 15/209,859

(22) Filed: Jul. 14, 2016

(65) Prior Publication Data

US 2017/0014330 A1    Jan. 19, 2017

Related U.S. Application Data

(60) Provisional application No. 62/192,125, filed on Jul. 14, 2015.

(51) Int. Cl.

| | |
|---|---|
| *A61Q 5/06* | (2006.01) |
| *A61K 8/91* | (2006.01) |
| *A61K 8/81* | (2006.01) |
| *A61K 8/891* | (2006.01) |
| *A45D 7/06* | (2006.01) |
| *A45D 20/04* | (2006.01) |
| *A46B 9/02* | (2006.01) |
| *A61K 8/02* | (2006.01) |
| *A61K 8/894* | (2006.01) |
| *C08F 283/12* | (2006.01) |
| *C08G 77/42* | (2006.01) |
| *A45D 7/00* | (2006.01) |

(52) U.S. Cl.
CPC .................. *A61K 8/91* (2013.01); *A45D 7/06* (2013.01); *A45D 20/04* (2013.01); *A46B 9/023* (2013.01); *A61K 8/0204* (2013.01); *A61K 8/8147* (2013.01); *A61K 8/891* (2013.01); *A61K 8/894* (2013.01); *A61Q 5/06* (2013.01); *C08F 283/12* (2013.01); *C08G 77/42* (2013.01); *A45D 2007/008* (2013.01); *A61K 2800/594* (2013.01); *A61K 2800/805* (2013.01)

(58) Field of Classification Search
None
See application file for complete search history.

(56) References Cited

U.S. PATENT DOCUMENTS

| | | | | |
|---|---|---|---|---|
| 2002/0012647 | A1* | 1/2002 | Cannell | A61K 8/442 424/70.23 |
| 2010/0111886 | A1* | 5/2010 | Verboom | A61K 8/731 424/70.122 |
| 2014/0237733 | A1* | 8/2014 | Zuedel Fernandes | A61Q 5/12 8/405 |
| 2015/0139931 | A1* | 5/2015 | Maekawa | A61Q 5/06 424/70.122 |
| 2015/0283060 | A1* | 10/2015 | Metten | A61Q 5/06 424/43 |

FOREIGN PATENT DOCUMENTS

| | | |
|---|---|---|
| EP | 2865693 A1 | 4/2015 |
| JP | 5649691 B2 | 1/2015 |
| JP | 2015-024977 A | 2/2015 |

OTHER PUBLICATIONS

International Search Report and Written Opinion dated Sep. 9, 2016 for Application No. PCT/US2016/042208, 10 pgs.
"Curl Lively Curls Hair Styling Foam," MINTEL, Dec. 1, 2014, 2 pgs., XP-002761002.
"Hair Styling Lotion for Hair Iron," MINTEL, Jul. 1, 2014, 2 pgs., XP-002761003.
WPI Database, Week 201515, Thomson Scientific, London, GB, Feb. 5, 2015, 2 pgs., XP-002761004.

* cited by examiner

*Primary Examiner* — Jyothsna A Venkat
(74) *Attorney, Agent, or Firm* — Frost Brown Todd LLC (57) ABSTRACT

Hairstyling compositions which provide the user with continuous wave frizz-free hairstyling using only low heat (such as that applied by a blow dryer) and a round hair brush as well as a natural feel to the hair is disclosed. The compositions incorporate a mixture of two and preferably three polymers, those polymers including an organopolysiloxane graft polymer, a graft polymer comprising polyacrylate (such as polyacrylate-32), and optionally a water-soluble silicone polymer (such as bis-PEG-8-dimethicone). The method of using these compositions to provide the desired hairstyles is also disclosed.

11 Claims, 1 Drawing Sheet

COMPOSITIONS FOR PROVIDING FRIZZ-FREE WAVY HAIRSTYLES USING LOW HEAT

This application claims priority from and is related to U.S. Provisional Patent Application No. 62/192,125, White and Steigerwald, filed Jul. 14, 2015, incorporated herein by reference.

BACKGROUND

Having appropriately styled hair is an important part of looking your best. However, there is always a trade-off between how the hair looks and how much time and money was invested in getting that hair style look. While some people are willing to spend a great deal of time achieving a certain look, most people, due to their busy schedules and work/family demands, want to get a stylish look for their hair without having to invest a great deal of time and money on an ongoing basis. The key, then, is to design a hair care product which provides the ability to achieve and maintain a comfortable/sophisticated hair style without requiring the investment of too much time and money on an ongoing basis.

A popular style is one in which the hair is relatively long and it comprises continuous hair bundles having a smooth wavy shape. Such styles are characterized as "smooth", "bouncy", and "flowing with movement". What is desired are long continuous waves, particularly at the ends of the hair, which are not frizzy and provide a soft look, where the hair has movement and volume.

The present invention is a hair care/hairstyle product which, when applied to hair, provides a durable, continuous bundle wave-shaping film which allows for the easy formation of desirable frizz-free waves by just using low heat (such as a blow dryer (about 70° C.)) together with the application of high styling force, such as from a round hair brush. This product has been found to provide the desired continuous wavy shape in an easy and highly repeatable manner, while leaving the hair looking and feeling natural.

SUMMARY

The present invention, therefore, defines a hairstyling composition comprising the following polymers in a hair care vehicle selected from water, alcohol, silicones, oils, hydrocarbons, esters, and combinations thereof:
- (a) from about 0.1% by weight to about 5% by weight of the composition of an organopolysiloxane graft polymer which includes an organopolysiloxane segment as a main chain thereof and an unsaturated monomer-derived polymer segment as a side chain thereof, in which the unsaturated monomer-derived polymer segment contains a repeating unit derived from N,N-dimethyl acrylamide (DMAAm), and the content of the organopolysiloxane segment in the organopolysiloxane graft polymer is not less than about 10% by weight and not more than about 70% by weight; and
- (b) from about 0.3% by weight to about 15% by weight of the composition of a graft polyacrylate polymer comprising polyacrylate as a main chain and having at least one organopolysiloxane as a side chain;

wherein the weight ratio of (a):(b) is from about 4:1 to about 1:4.

In addition to that composition, the present invention also encompasses hairstyling compositions as described above but which also include the following additional polymer component:
- (c) from about 0.1% by weight to about 5% by weight of the composition of a water-soluble silicone polymer which helps to blend polymers (a) and (b) (preferably one which is comprised of a linear inorganic backbone of silicone and oxygen having organic pendant groups, said pendant groups containing multiple units of ethylene glycol in an amount so as to render the polymer water-soluble);

wherein the weight ratio of (a):(b) is from about 4:1 to about 1:4, and the weight ratio of (b):(c) is from about 1:4 to about 4:1.

The present application also encompasses a method for providing gentle wave frizz-free hairstyles using the compositions defined herein, comprising the following steps:
- (a) wetting the hair of the subject, for example, by applying shampoo and/or conditioner to the hair of the subject;
- (b) towel-drying the hair;
- (c) applying a composition of the present invention to the wet hair of step (b); and
- (d) applying low heat and high force brushing to the hair (such as by using a blow dryer and a round hair brush) to achieve the desired hairstyle.

All percentages and ratios stated herein are "by weight", unless otherwise specified. Further, any patents, patent applications or other publications, discussed herein, are incorporated by reference in this application, unless otherwise stated.

DETAILED DESCRIPTION

To achieve the desired goal, as described above, Applicants use styling polymers which have high tensile strength, as well as elasticity and flexibility; these polymers will be described below. In addition, the resulting combination of polymers, and the composition it is formulated into, must be easy to apply (e.g., easy to spray) and not provide a heavy coated feel to hair (i.e., it must allow hair to retain a natural feel). The focus here is on polymers which have a low $T_g$ (glass transition temperature), as well as a high tensile strength.

Creating wavy shapes in hair is a physical challenge due to the low heat and strong torsional forces of the daily styling process. Due to their high $T_g$, conventional styling polymers require high heat from the use of a curling iron or flat iron to effectively style the hair. These same polymers also tend to shatter or are brittle and will fracture when strong torsional forces are applied, as is the case when a round brush is used by a consumer to style the hair. Current technologies used for the purpose of styling tend to create stiff and brittle films. These films, when used on the hair, tend to exhibit low durability; they break when they are exposed to high mechanical forces. Once the film breaks, there is a loss of the intended shape that was created (i.e., curls or waves) and misalignment or what is known as hair frizz may form.

The present invention uses low $T_g$ polymers which do not require high heat in order to become more elastic and can change the shape of the hair at such lower temperatures. Since the invention is a film with high tensile strength, it will not fracture when a round brush/high force is applied. The use of such low $T_g$/high tensile strength films is unique in hair care compositions.

The purpose of the present invention, therefore, is to provide to a consumer the ability to create a frizz-free wavy hairstyle by using just a blow dryer and a round (cylindrical) hair brush. The invention entails the delivery of a low $T_g$/high tensile strength polymer film to the hair which is made up of three classes of polymers, which include polysilicone-28, polyacrylate-32 and (optionally) bis-PEG-8-dimethicone, as examples. This polymer combination provides a highly flexible (low $T_g$) film that also exhibits high tensile strength. The method of delivery can be by any known hair care composition, but is preferably a non-aerosolized pump spray in order to allow for uniform deposition on the hair surface. The polymer blend only requires low heat shaping due to the incorporation of two low $T_g$ polymers (polysilicone-28 and bis-PEG-8-dimethicone). Polyacrylate-32, a polymer which exhibits high tensile strength, prevents the film from fracturing during the heating process and mechanical interaction with the hair brush.

Organopolysiloxane Graft Polymer (Polymer (a))

Siloxane graft polymers which are utilized in the present invention are described in Japanese Patent Application JP2013-118309, Kao Corporation, filed Jun. 4, 2013, incorporated herein by reference. This graft polymer contains an organopolysiloxane segment as a main chain thereof.

The chemical structure of the organopolysiloxane segment is not particularly limited. Specific examples of the preferred organopolysiloxane segments include modified organopolysiloxane segments represented by the following general formulas (1) or (2).

In the above general formulae (1) and (2), $R^1$ groups are each independently an alkyl group having not less than 1 and not more than 22 carbon atoms or an aryl group having not less than 6 and not more than 14 carbon atoms; and $R^2$ groups are each an alkylene group that may contain a hetero atom. Also, p is a number of not less than 2 and not more than 4,000, and q is a number of not less than 2 and not more than 250. In the general formulae (1) and (2), the repeating p units and the repeating q units may be bonded to each other either in a block form or in a random form.

In the above general formulae (1) and (2), the alkyl group represented by $R^1$ is a straight-chain alkyl group, a branched-chain alkyl group or a cyclic alkyl group. The number of carbon atoms of the alkyl group represented by $R^1$ is preferably not less than 1 and not more than 10, and more preferably not more than 6 from the viewpoint of good water dispersibility of the graft polymer of the present invention. Specific examples of the alkyl group represented by $R^1$ include a methyl group, an ethyl group, an n-propyl group, an isopropyl group, an n-butyl group, a tert-butyl group, a pentyl group, a hexyl group, a cyclohexyl group, a heptyl group, an octyl group, a nonyl group, a decyl group, an undecyl group, a dodecyl group, an octadecyl group, a nonadecyl group, an eicosyl group and a docosyl group. Meanwhile, the water dispersibility of the graft polymer means such a property that the graft polymer can be stably dispersed in a composition containing water as a main component. When the graft polymer has a good water dispersibility, it is possible to compound the graft polymer in a hair cosmetic containing water as main solvent, so that the hair cosmetic can exhibit a good shampooing property.

The number of carbon atoms of the aryl group represented by $R^1$ is preferably not less than 6 and not more than 12, and more preferably not more than 9 from the viewpoint of good water dispersibility of the graft polymer of the present invention. Specific examples of the aryl group represented by $R^1$ include a phenyl group, a tolyl group, a xylyl group, a naphthyl group, a biphenyl group, an anthryl group and a phenanthryl group.

Of these aryl groups as $R^1$, from the viewpoint of a good water dispersibility of the graft polymer used in the present invention, preferred are straight-chain or branched-chain alkyl groups having not less than 1 and not more than 6 carbon atoms, more preferred are straight-chain or branched-chain alkyl groups having not less than 1 and not more than 3 carbon atoms, and still more preferred is a methyl group.

In the above general formulae (1) and (2), p is a number of not less than 2 and not more than 4,000, and q is a number of not less than 2 and not more than 250.

From the viewpoint of a good touch feeling (less stickiness) of hair after setting the hair with a hair cosmetic using the organopolysiloxane graft polymer herein, p is preferably a number of not less than 50, more preferably not less than 80, and still more preferably not less than 100, and from the viewpoint of a good water dispersibility of the graft polymer of the present invention, p is also preferably a number of not more than 2,000, more preferably not more than 1,300, and still more preferably not more than 700.

From the viewpoint of good water dispersibility of the graft polymer of the present invention, q is preferably a number of not less than 3, and more preferably not less than 5, and from the viewpoint of good hair setting property of the hair cosmetic of the present invention and good hair style retentivity thereof after the setting, q is also preferably a number of not more than 50, and more preferably not more than 30.

In the above general formulae (1) and (2), a part or whole of the alkylene group ($R^2$) which may contain a hetero atom is bonded to both the main chain and the unsaturated monomer-derived polymer segment to function as a connecting group between the main chain and the unsaturated monomer-derived polymer segment as the side chain. In the case where any alkylene group that may contain a hetero atom is present in the form of a group unbonded to the unsaturated monomer-derived polymer segment, the alkylene group that may contain a hetero atom is bonded to the main chain and a hydrogen atom.

In the present invention, the number of carbon atoms of the alkylene group that may contain a hetero atom is preferably not less than 2, and more preferably not less than 3, from the viewpoint of a good availability of the raw materials used upon production of the graft polymer herein. Also, from the viewpoint of good water dispersibility of the graft polymer herein, the number of carbon atoms of the alkylene group that may contain a hetero atom is preferably not more than 20, more preferably not more than 10, and still more preferably not more than 8.

In the present invention, the alkylene group that may contain a hetero atom may be interrupted by at least one atom or functional group selected from the group consisting of an oxygen atom, a sulfur atom, —NH—, —COO—, —NHCO— and —NR³CO—. That is, the alkylene group that may contain a hetero atom may have a structure constituted of "-(an alkylene group portion 1)-(the above atom or functional group)-(an alkylene group portion 2)". In this case, the number of carbon atoms of the alkylene group means a sum of the number of carbon atoms of the alkylene group portion 1 and the number of carbon atoms of the alkylene group portion 2. In the above —NR³CO—, R³ is an alkyl group having not less than 1 and not more than 3 carbon atoms. When the alkylene group that may contain a hetero atom is interrupted by the above atom or functional group, from the viewpoint of facilitated production of the graft polymer herein, the alkylene group that may contain a hetero atom is preferably interrupted by —NHCO—.

In the present invention, the alkylene group that may contain a hetero atom may be substituted with at least one monovalent group selected from the group consisting of a hydroxyl group, an amino group, a ($C_1$-$C_3$) alkyl amino group, a di-($C_1$-$C_3$) alkyl amino group, an amide group obtained by dehydration condensation of an amino group and a fatty acid having not less than 2 and not more than 4 carbon atoms, a carboxyl group, and a ($C_1$-$C_3$) alkyl ester group. In this case, the number of carbon atoms of the alkylene group that may contain a hetero atom does not include the number of carbon atoms contained in the above substituent group. From the viewpoint of a good availability of the raw materials upon production of the graft polymer herein, the alkylene group that may contain a hetero atom is preferably substituted with at least one monovalent group selected from the group consisting of an acetamide group, a ($C_1$-$C_3$) alkyl amino group and an amine group.

In the present invention, the alkylene group that may contain a hetero atom may be substituted with a divalent hetero atom or a divalent group containing a hetero atom selected from the group consisting of —O—, —S—, —NH—, —NR³⁰—, and —COO—, in which $R^{30}$ is a ($C_1$-$C_3$) alkyl group that may be substituted with a dimethyl amino group. The divalent hetero atom or the divalent group containing a hetero atom is bonded to the unsaturated monomer-derived polymer segment when the alkylene group that may contain a hetero atom functions as a connecting group to the unsaturated monomer-derived polymer segment, and in other cases, the divalent hetero atom or the divalent group containing a hetero atom is bonded to a hydrogen atom.

From the viewpoint of facilitated production of the graft polymer herein, the alkylene group that may contain a hetero atom is preferably substituted with —S—.

The alkylene group ($R^2$) which may contain a hetero atom is preferably bonded to the unsaturated monomer-derived polymer segment through the hetero atom, more preferably through a nitrogen atom, an oxygen atom or a sulfur atom, and still more preferably through a sulfur atom.

Therefore, the "alkylene group that may contain a hetero atom" represented by $R^2$ corresponds to (i) an unsubstituted alkylene group; (ii) an alkylene group interrupted by at least one atom or functional group selected from the group consisting of an oxygen atom, a sulfur atom, —NH—, —COO—, —NHCO—, and —NR³⁰CO—; (iii) an alkylene group substituted with at least one monovalent group selected from the group consisting of a hydroxyl group, an amino group, a ($C_1$-$C_3$) alkyl amino group, a di-($C_1$-$C_3$) alkyl amino group, an amide group obtained by dehydration condensation of an amino group and a fatty acid having not less than 2 and not more than 4 carbon atoms, a carboxyl group, and a ($C_1$-$C_3$) alkyl ester group; (iv) an alkylene group substituted with a divalent hetero atom or a divalent group containing a hetero atom selected from the group consisting of —O—, —S—, —NH—, —NR³⁰—, and —COO—; and an alkylene group in the form of a combination of the above (ii), (iii) and (iv).

Specific examples of the alkylene group that may contain a hetero atom as used in the present invention include those group represented by the following formulae (i) to (xii). Of these groups, from the viewpoint of facilitated production of the graft polymer of the present invention, preferred are those groups represented by the following formulae (xi) and (xii).

In the formulae (i) to (xii), "*" represents a moiety bonded to the silicon atom in the general formula (1) or (2), whereas "**" represents a moiety bonded to the unsaturated monomer-derived polymer segment.

In the formula (xii), $X^1$ is at least one group selected from the group consisting of —O—, —COO—, —COO—, —CONH—, and —NHCO—. Of these groups, from the viewpoint of facilitated production of the graft polymer herein, preferred are —CONH— and —NHCO—, and more preferred is —NHCO—.

Also, in the formula (xii), $R^4$ is an alkylene group that may be substituted with at least one monovalent group selected from the group consisting of a hydroxyl group, an amino group, a ($C_1$-$C_3$) alkyl amino group, a di-($C_1$-$C_3$) alkyl amino group, an amide group obtained by dehydration condensation of an amino group and a fatty acid having not less than 2 and not more than 4 carbon atoms, a carboxyl group, and a ($C_1$-$C_3$) alkyl ester group. Of these substituent groups, from the viewpoint of a good availability of the raw materials upon production of the graft polymer herein, preferred are an acetamide group, a ($C_1$-$C_3$) alkyl amino group and an amino group. The number of carbon atoms of the alkylene group represented by $R^4$ is preferably not less than 2 and more preferably not less than 3, from the viewpoint of facilitated production of the graft polymer herein, and also is preferably not more than 10, and more preferably not more than 6, from the viewpoint of a good water dispersibility of the graft polymer herein.

Specific examples of $R^4$ include those groups represented by the following formulae (xiii) to (xv).

(xiii)

n = 2~4

(xiv)

(xv)

In the formula (xiv), $X^-$ represents an anion selected from the group consisting of a halide ion, such as a chloride ion and a bromide ion, an acetate ion and a ($C_1$-$C_3$) alkyl sulfate ion.

Unsaturated Monomer-Derived Polymer Segment

The organopolysiloxane graft polymer used in the present invention contains an unsaturated monomer-derived polymer segment as a side chain thereof. From the viewpoint of good water dispersibility of the graft polymer herein, the unsaturated monomer-derived polymer segment can contain a repeating unit derived from DMAAm in an amount of not less than 50% by weight, preferably not less than 70% by weight, and more preferably not less than 75% by weight. Also, from the viewpoint of reducing stickiness of hair after setting the hair using the hair cosmetic of the present invention, the content of the repeating unit derived from DMAAm in the unsaturated monomer-derived polymer segment is not more than 100% by weight, preferably not more than 95% by weight, and more preferably not more than 90% by weight.

The repeating unit derived from the unsaturated monomer as used herein means a repeating unit formed upon polymerization of the unsaturated monomer.

In the graft polymer herein, the content of the repeating unit derived from DMAAm in the unsaturated monomer-derived polymer segment may be measured by an NMR method.

The moiety other than the repeating unit derived from DMAAm in the unsaturated monomer-derived polymer segment is made up of a repeating unit derived from an unsaturated monomer (except for DMAAm) capable of copolymerizing with DMAAm. Examples of the repeating unit derived from the unsaturated monomer capable of copolymerizing with DMAAm include those repeating units derived from unsaturated monomers such as olefins, halogenated olefins, vinyl esters, (meth)acrylic acid esters, and (meth)acrylamides (except for DMAAm). The moiety other than the repeating unit derived from DMAAm in the unsaturated monomer-derived polymer segment may be constituted of either a repeating unit derived from a single kind of unsaturated monomer capable of copolymerizing with DMAAm, or a repeating unit derived from two or more kinds of unsaturated monomers capable of copolymerizing with DMAAm.

Specific examples of the olefins include ethylene, propylene and isobutylene. Specific examples of the halogenated olefins include vinyl chloride, vinyl fluoride, vinylidene chloride and vinylidene fluoride. Specific examples of the vinyl esters include vinyl formate, vinyl acetate, vinyl propionate and vinyl versatate.

Specific examples of the (meth)acrylic acid esters include (meth)acrylic acid esters containing an alkyl group having not less than 1 and not more than 16 carbon atoms such as methyl (meth)acrylate, ethyl (meth)acrylate, propyl (meth)acrylate, isobutyl (meth)acrylate, n-butyl (meth)acrylate, tert-butyl (meth)acrylate, hexyl (meth)acrylate, octyl (meth) acrylate, 2-ethylhexyl (meth)acrylate, decyl (meth)acrylate, dodecyl (meth)acrylate and cyclohexyl (meth)acrylate; (meth)acrylic acid esters containing an alkyl group having not less than 1 and not more than 16 carbon atoms which is substituted with a hydroxyl group, such as 2-hydroxyethyl (meth)acrylate; and polyethylene glycol (meth)acrylate, polyethylene glycol monomethyl ether (meth)acrylate, etc.

Specific examples of the (meth)acrylamides except for DMAAm include (meth)acrylamides such as acrylamide and methacrylamide; N,N-dialkyl (meth)acrylamides (except for DMAAm) such as N,N-diethyl (meth)acrylamide; N-alkyl (meth)acrylamides such as N-isopropyl (meth)acrylamide, N-tert-butyl (meth)acrylamide, N-cyclohexyl (meth)acrylamide and N-tert-octyl (meth)acrylamide; N-mono-substituted (meth)acrylamides containing a carbonyl group in a substituent group bonded to a nitrogen atom thereof, such as diacetone (meth)acrylamide; N-mono-substituted (meth)acrylamides containing an amino group in a substituent group bonded to a nitrogen atom thereof, such as N,N-dimethylaminopropyl (meth)acrylamide; and N-mono-substituted (meth)acrylamides containing a hydroxyl group in a substituent group bonded to a nitrogen atom thereof, such as N-methylol (meth)acrylamide and N-hydroxyethyl (meth)acrylamide.

Of these unsaturated monomers, from the viewpoint of good hair setting property and good hair style retentivity after the hair setting, preferred are (meth)acrylamides except for DMAAm and/or (meth)acrylates; more preferred are acrylamide, methacrylamide, N,N-diethyl (meth)acrylamide, N-isopropyl (meth)acrylamide, N-tert-butyl (meth)acrylamide, diacetone (meth)acrylamide (t-BuAAm), N,N-dimethylaminopropyl (meth)acrylamide, N hydroxyethyl (meth) acrylamide, N-methylol (meth)acrylamide, methyl (meth) acrylate, ethyl (meth)acrylate, propyl (meth)acrylate, isobutyl (meth)acrylate, n-butyl (meth)acrylate, tert-butyl (meth)acrylate and 2-hydroxyethyl (meth)acrylate; still more preferred are N-tert-butyl (meth)acrylamide (t-BuAAm), N-hydroxyethyl (meth)acrylamide, diacetone (meth)acrylamide, methyl (meth)acrylate, ethyl (meth)acrylate, tert-butyl (meth)acrylate and N,N-dimethylaminopropyl (meth)acrylamide; even still more preferred are N-tert-butyl (meth)acrylamide, N-hydroxyethyl (meth)acrylamide, diacetone (meth)acrylamide, methyl (meth)acrylate, ethyl (meth)acrylate and tert-butyl (meth)acrylate; and further even still more preferred is N-tert-butyl (meth)acrylamide.

Construction of Organopolysiloxane Graft Polymer

The content of the organopolysiloxane segment in the graft polymer of the present invention is not less than 10% by weight, preferably not less than 20% by weight, and more preferably not less than 30% by weight, from the viewpoint of reducing stickiness of hair after setting the hair using the hair cosmetic of the present invention, and is also not more than 70% by weight, and preferably not more than 60% by weight, from the viewpoint of good water dispersibility of the graft polymer herein.

The content of the organopolysiloxane segment in the graft polymer of the present invention may be measured by an NMR method.

In addition, from the viewpoint of attaining good water dispersibility of the graft polymer herein and reducing stickiness of hair after setting the hair using the hair cosmetic of the present invention, the weight ratio (in the polymer) (a/b) of the organopolysiloxane segment (a) to the unsaturated monomer-derived polymer segment (b) is preferably not less than 10/90, more preferably not less than 20/80, still more preferably not less than 30/70, and even still more preferably not less than 35/65, and is also preferably not more than 70/30, more preferably not more than 60/40.

Meanwhile, in the present specification, when the graft polymer of the present invention is produced from the below-mentioned radical-reactive organopolysiloxane, the above mass ratio (a/b) is regarded as being the same as a ratio (c/(d−e)) of a "total amount (c) of the radical-reactive organopolysiloxane charged upon production of the graft polymer" to a value obtained by subtracting a "total amount (e) of a polymer derived from an unsaturated monomer which is unbonded to the organopolysiloxane produced upon production of the graft polymer" from a "total amount (d) of the unsaturated monomer charged upon production of the graft polymer" (the following formula (I)).

$$a/b = c/(d-e) \quad \quad (I)$$

The number-average molecular weight (MNg) of the organopolysiloxane segment being present between the adjacent unsaturated monomer-derived polymer segments (hereinafter also referred to merely as a "molecular weight between graft points") is preferably not less than 500, more preferably not less than 700, still more preferably not less than 1,000, and even still more preferably not less than 1,500, from the viewpoints of attaining a good hair setting property when setting the hair with a hair cosmetic containing the organopolysiloxane graft polymer herein and improving a hair style retentivity after the setting, and is also preferably not more than 10,000, more preferably not more than 5,000, still more preferably not more than 3,000, and even still more preferably not more than 2,500, from the viewpoint of attaining a good water dispersibility of the graft polymer herein.

The "organopolysiloxane segment being present between the adjacent unsaturated monomer-derived polymer segments" as used herein means a portion surrounded by a broken line as shown in the following formula which is located between a bonding point (bonding point A) at which the unsaturated monomer-derived polymer segment is bonded to the organopolysiloxane segment and a bonding point (bonding point B) at which the unsaturated monomer-derived polymer segment adjacent to the above polymer segment is bonded to the organopolysiloxane segment, and is constituted of one $R^1SiO$ unit, one $R^2$ group and $R^1{}_2SiO$ units in the number of y+1.

(3)

In the above formula, $R^1$ groups are each independently an alkyl group having not less than 1 and not more than 22 carbon atoms or an aryl group having not less than 6 and not more than 14 carbon atoms; $R^2$ groups are each an alkylene group that may contain a hetero atom; —W—$R^5$ groups are each an unsaturated monomer-derived polymer segment in which $R^5$ is a residue of a polymerization initiator or a hydrogen atom; and y is a positive number.

The molecular weight between graft points is an average value of molecular weights of the portions surrounded by a broken line in the above formula, and may be construed as a mass (g/mol) of the organopolysiloxane segment per one mole of the unsaturated monomer-derived polymer segment. In the case where the graft polymer of the present invention is produced from a radical-reactive organopolysiloxane, and all of the radical-reactive functional groups are bonded to the unsaturated monomer-derived polymer segment, the molecular weight between graft points is also regarded as being identical to an inverse number of a molar number (mol/g) of the radical-reactive functional groups that are present per a unit mass of the radical-reactive organopolysiloxane.

In addition, the weight-average molecular weight (MWsi) of the organopolysiloxane segment constituting the main chain of the graft polymer is preferably not less than 3,000, more preferably not less than 5,000, still more preferably not less than 10,000, and even still more preferably not less than 15,000, from the viewpoint of a good hair setting property when setting the hair using a hair cosmetic containing the organopolysiloxane graft polymer herein and a good hair style retentivity after the setting. Also, MWsi is preferably not more than 200,000, more preferably not more than 100,000, still more preferably not more than 60,000, and even still more preferably not more than 50,000, from the viewpoint of a good water dispersibility of the graft polymer of the present invention.

In the case where the organopolysiloxane graft polymer herein is produced from the below-mentioned radical-reactive organopolysiloxane, the organopolysiloxane segment has a structure common to that of the radical-reactive organopolysiloxane, and therefore MWsi is substantially the same as a weight-average molecular weight (MWra) of the radical-reactive organopolysiloxane. For this reason, in the present invention, MWsi is regarded as being the same as MWra. Meanwhile, MWra is a value calculated in terms of a polystyrene from such a molecular weight as measured by gel permeation chromatography (GPC).

The weight-average molecular weight (MWt) of the graft polymer of the present invention is preferably not less than 10,000, more preferably not less than 14,000, still more preferably not less than 17,000, and even still more preferably not less than 30,000, from the viewpoints of a good hair setting property when setting the hair using a hair cosmetic containing the organopolysiloxane graft polymer herein and a good hair style retentivity after the setting. Also, MWt is preferably not more than 200,000, more preferably not more than 160,000, still more preferably not more than 130,000, and even still more preferably not more than 95,000, from the viewpoint of a good water dispersibility of the graft polymer of the present invention. When MWt falls within the above-specified range, it is possible to ensure a sufficient strength of a film obtained from the graft polymer, and the resulting graft polymer can exhibit an excellent water dispersibility and can be further improved in hair setting property and hair style retentivity after setting without stickiness.

In the present specification, MWt is a value calculated in terms of a polystyrene from such a molecular weight as measured by GPC.

In addition, when producing the graft polymer herein from the radical-reactive organopolysiloxane, the weight-average molecular weight as a calculated value (MWtcalc) of the graft polymer herein which is calculated from MWra and an inverse number of the above mass ratio (a/b) according to the following formula (II), is preferably not less than 10,000, more preferably not less than 14,000, still more preferably not less than 17,000, and even still more preferably not less than 30,000, from the viewpoint of a good hair setting property when setting the hair using a hair cosmetic containing the organopolysiloxane graft polymer herein and a good hair style retentivity after the setting. Also, MWtcalc is preferably not more than 200,000, more preferably not more than 160,000, still more preferably not more than 130,000, and even still more preferably not more than 95,000, from the viewpoint of a good water dispersibility of the graft polymer herein.

$$MWtcalc = MWra + \{1 + \text{mass ratio}(b/a)\} \quad (II)$$

An example of making the organopolysiloxane graft polymer described herein (Component (a)) is as follows:

SYNTHESIS EXAMPLE I

Synthesis of Radical-Reactive Organopolysiloxane A

A separable flask equipped with a reflux condenser, a thermometer, a nitrogen inlet tube and a stirrer was charged with 100 g of a side-chain primary aminopropyl-modified organopolysiloxane (weight-average molecular weight: 30,000; number of moles of an amino group per a unit mass thereof: 1/2,030 mol/g; available from Dow Corning Toray Co., Ltd.) as a reactive functional group-containing organopolysiloxane and 8 g of N-acetyl-DL-homocysteine thiolactone. The contents of the flask were heated to 100° C. and stirred for 3 h in a nitrogen atmosphere, thereby synthesizing a sulfanyl group-containing radical-reactive organopolysiloxane A. As a result of subjecting the resulting reaction solution to potentiometric titration measurement to determine a residual amount of an amino group remaining in the reaction solution, it was confirmed that 99% of the amino group of the side-chain primary aminopropyl-modified organopolysiloxane as the raw material was reacted with N-acetyl-DL-homocysteine thiolactone (conversion rate of amino group: 99%). Therefore, the number of moles of the sulfanyl group per a unit mass of the radical-reactive organopolysiloxane A was 1/2,210 mol/g. As a result of subjecting the radical-reactive organopolysiloxane A to GPC measurement, it was confirmed that the radical-reactive organopolysiloxane A had a weight-average molecular weight of 30,000.

TABLE 1

| | Synthesis Example | 1 |
|---|---|---|
| Side-chain primary aminopropyl-modified organopolysiloxane | Weight-average molecular weight | 30,000 |
| | Number of moles of amino group (mol/g) | 1/2,030 |
| Conversion rate of amino group by reaction (%) | | 99 |
| Radical-reactive organopolysiloxane | Name | A |
| | Weight-average molecular weight | 30,000 |
| | Number of moles of sulfanyl group$^2$) (mol/g) | 1/2,210 |

Synthesis of Organopolysiloxane Graft Polymer E

A separable flask equipped with a reflux condenser, a thermometer, a nitrogen inlet tube and a stirrer was charged with 101.0 g of ethanol. While stirring the ethanol under reflux at 80° C. in a nitrogen atmosphere, the following solutions (a) and (b) were respectively charged in separate dropping funnels and added dropwise at the same time to the flask over 1 h.

Solution (a): Solution prepared by mixing 76.8 g of DMAAm, 19.2 g of N-tert-butyl acrylamide (hereinafter referred to as "t-BuAAm") and 96.0 g of ethanol.

Solution (b): Solution prepared by mixing 64.0 g of the radical-reactive organopolysiloxane A synthesized in the above Synthesis Example 1, 0.03 g of 2,2'-azobis(2,4-dimethyl valeronitrile) "V-65B" (available from Wako Pure Chemical Industries, Ltd.; azo-based polymerization initiator) and 43.0 g of ethanol.

After completion of the dropwise addition, the reaction mixture was stirred at 80° C. for 3 h, and then cooled. The obtained reaction time was 4 h in total. The reaction mixture was allowed to stand at room temperature (25° C.) under reduced pressure (20 kPa) over 4 h to remove ethanol therefrom, thereby obtaining a mixture containing an organopolysiloxane graft polymer E as a white solid. As a result of measuring a sulfanyl group residual rate of the resulting product by the above method, it was confirmed that the sulfanyl group residual rate was 3%.

The content of the unsaturated monomer-derived polymer that was unbonded to the organopolysiloxane graft polymer in the mixture containing the organopolysiloxane graft polymer E obtained after completion of the reaction was measured by the above method. As a result, it was confirmed that the content of the unbonded polymer in the mixture was 29% by mass. The mass ratio (a/b) of the organopolysiloxane segment (a) to the unsaturated monomer-derived polymer segment (b) in the organopolysiloxane graft polymer E was calculated from the above formula (I). As a result, it was confirmed that the mass ratio (a/b) was 56/44.

The resulting mixture containing the organopolysiloxane graft polymer E was purified by silica gel column chromatography (eluent: methanol/chloroform=15/85 (v/v)), thereby obtaining the organopolysiloxane graft polymer E as a white solid. The thus isolated organopolysiloxane graft polymer E was subjected to the above nuclear magnetic resonance ($^1$H-NMR) analysis to determine a mass ratio (a/b) of the organopolysiloxane graft polymer E. As a result, it was confirmed that the mass ratio (a/b) was 56/44 and therefore was identical to the above calculation result. As a result of subjecting the isolated organopolysiloxane graft polymer E to GPC measurement, it was confirmed that the weight-average molecular weight thereof was 63,000.

The hairstyling composition of the present invention contains the graft polymer described above (hereinafter also referred to as a "component (a)"). By incorporating the graft polymer of the present invention into the hairstyling composition, it is possible to attain a soft touch, a hairstyling property that is that remains reasonably constant even upon combing of hand or fingers through hair, and a more natural finish feeling.

In preferred embodiments, these organopolysiloxane graft polymers include two or more side chains which are respectively bonded to an optional silicon atom in the organopolysiloxane segment constituting the main chain of the graft polymer through an alkylene group containing a hetero atom.

Further preferred organopolysiloxane graft polymers of the present invention include segments having one or both of the following formulas:

wherein $R^1$ is each independently $C_1$-$C_{22}$ alkyl or $C_6$-$C_{14}$ aryl; $R^2$ are each alkylene groups that may contain a hetero atom; p is from about 2 to about 4,000; and q is from about 2 to about 250; wherein the repeating p units and the repeating q units may be bonded to each other either in block form or in random form.

These polymers exhibit visco-elasticity when used with (relatively low temperature) blow dry heat. The present compositions contain from about 0.1% to about 5%, by weight, and preferably from about 2% to about 4% by weight of the organosiloxane graft polymer defined herein.
Polyacrylate Graft Polymer (Component (b))

The second polymer which is utilized in the compositions of the present invention is a graft polymer comprising polyacrylate as the main chain and having at least one organopolysiloxane as a side chain (Component (b)). The polymer exhibits a high tensile strength. The polymer is preferably anionic. This polymer is utilized at from about 0.3% to about 15% by weight (preferably from about 6% to about 12% by weight) of the finished composition. The polyacrylate graft polymer has a high tensile strength (i.e., when a stretching force is applied to the polymer film, the film is able to resist maximum stress before failing/breaking), and a glass transition temperature ($T_g$) of from about 85° C. to about 95° C. Glass transition temperature ($T_g$) is the temperature region where a polymer transitions from a hard, glassy material to a soft, rubbery material. The polymer is an acrylate-based polymer. An example of such a polymer is polyacrylate-32, which has a $T_g$ of 92° C. and is a hard type polymer that exhibits high tensile strength. Specifically, polyacrylate-32 is the copolymer of PEG-PPG-23/6 dimethicone, sodium acryloyldimethyltaurate, citraconic anhydride, and one or more monomers of acrylic acid, methacrylic acid, and esters thereof.
Water-Soluble Silicone Polymer (Component (c))

The third polymer (component (c)), which may be used in the present invention, is a water-soluble silicone polymer which helps to blend components (a) and (b) together and into the composition, and preferably which is comprised of a linear inorganic backbone containing silicone and oxygen and having organic pendent groups, said pendent groups containing multiple units of ethylene glycol in an amount so as to render the polymer water-soluble. The inclusion of this third polymer is optional in the present invention, although it is preferred to be included. When included, this third polymer can comprise from about 0.1% to about 5%, preferably from about 0.5% to about 2%, by weight of the finished hair care composition. In some embodiments, the water-soluble silicone polymer utilized in the present invention has a dimethicone backbone, and preferably is a $(PEG)_x$ dimethicone, wherein x is from about 6 to about 20, preferably from about 8 to about 10. It is the level of PEG in the molecule which provides water-solubility to the polymer. An example of a water-soluble silicone polymer utilizable in the present invention is bis-PEG-8-dimethicone.

By "blending components (a) and (b)" is meant that component (c) helps create a more uniform film (e.g., on the hair) which better incorporates the properties of both component (a) and component (b) into one film (i.e., a film with both low $T_g$ and high tensile strength).

Examples of other water-soluble silicone polymers which may be utilized in the present invention include the following:

Dimethicone n = 2-2,000

Amino-functionalized PDMS (Polydimethylsiloxane)—for Example, amodimethicone

The three polymers, described above, are utilized in the compositions of the present invention in defined ratios. Specifically, referring to the organosiloxane graft polymer as polymer (a), the polyacrylate graft polymer as polymer (b), and the water-soluble silicone polymer as polymer (c), the following ratios are utilized in formulating the present compositions: the ratio of (a):(b), by weight, is from about 4:1 to about 1:4, and the weight ratio of polymer (b):(c), is from about 1:4 to about 4:1. In certain embodiments of the present invention, the weight ratio of (a):(b) is from about 3:1 to about 1:3, and the weight ratio of (b):(c) is from about 1:3 to about 3:1. In preferred embodiments, the amount (by weight) of polymer (b) in the composition is greater than the amount of polymer (a). In preferred embodiments, the weight ratio of the polymers (a):(b):(c) is from about 1:1:1 to about 1:4:1, preferably about 1:3:1. Changing this ratio may allow for an increase in the tensile properties of the film, for example, doubling the polyacrylate-32 ratio with respect to polysilicone-28 and bis-PEG-8-dimethicone. Changing the amount of polyacrylate-32 may also reduce the elasticity of the film which may be desired for curly shapes which have a higher degree of curvature. When calculating these ratios, it is important that they be based on the presence of the actual polymer in the composition and not based on an included solvent. This is illustrated in the examples below.

The hair care vehicles that may be used in formulating the compositions of the present invention are those typically used in hair care compositions and are well-known in the art. Those vehicles are selected from water, alcohol, silicones, oils, hydrocarbons, esters, and combinations thereof. The vehicle typically comprises from about 5% to about 95%, preferably from about 30% to about 90%, of the total composition.

The formulated product of the present invention has a product pH of from about 5 to about 8, preferably from about 6 to about 7.

The compositions of the present invention may be formulated as any of a group of hairstyling compositions well-known in the art, such as shampoos, conditioners, aerosol styling sprays, non-aerosol styling sprays, gels, and emulsions. Of these formulation possibilities, non-aerosol styling sprays are preferred because they tend to provide the most convenient way to achieve uniform coverage of the composition when applied to hair.

These compositions, as well as their manner of formulation and additional components utilized in their formulation, are conventional and are well-known to those skilled in the art. Additional components conventionally utilized in hair care compositions may be used in the compositions of the present invention to achieve their known benefits when used at their conventional usage levels. An exemplary non-inclusive list of such additional components includes preservatives, pH adjustment agents, buffer agents, colorants, fragrances, neutralization materials, surfactants, emulsifiers, humectants, and anti-static agents, emollients, hair conditioning polymers, thickening agents/polymers, and combinations thereof. The compositions are formulated by mixing the individual components together, as would be well-known to those skilled in the art. Since polymer (b) is a polyacrylate anionic polymer, it requires neutralization prior to its inclusion in the composition. A material frequently used for such neutralization is aminomethyl propanol (AMP), although other basic neutralizing agents, such as hydroxides or amines, can also be used.

In the method of using the compositions of the present invention, the composition is applied to the hair (such as by spraying it onto the hair) and low heat is applied to the hair (such as by a blow dryer) together with high force brushing in order to achieve the desired hairstyle. The low heat is typically delivered by a blow dryer (expelling air at a temperature of from about 60 to about 80° C.) and the brushing is typically accomplished by using a round (cylindrical) styling hairbrush. Specifically, when the hairspray version of the present invention is utilized the following steps are typically followed:

(a) the hair of the consumer is wetted; for example, a shampoo and/or conditioner is applied to the hair of the consumer (and rinsed out or left in the hair, as appropriate);

(b) the hair is towel-dried;

(c) the composition of the present invention is applied (e.g., sprayed) onto the wet hair of step (b); and (d) low heat is applied to the treated hair together with high force brushing to achieve the desired hairstyle.

Generally, when applied, from about 0.5 to about 8 grams (i.e., a "styling effective amount") of the hairstyling composition is applied to the hair prior to styling.

FORMULATIONAL EXAMPLE 1

A non-aerosol spray version of a composition of the present invention is made using the following ingredients:

| INCI | | wt/wt % |
|---|---|---|
| Water | | 83.960 |
| Polyacrylate-32 | Lubrizol | 9.000 |
| AMP | | 0.800 |
| Polysilicone-28 | Kao | 3.000 |
| Bis-Peg-8 Dimethicone | Grant | 1.000 |
| Methyl Paraben | | 0.11 |
| Propyl Paraben | | 0.03 |
| Ethanol | | 2.00 |
| Fragrance | | 0.10 |

| Polymer | Activity | Formula Activity |
|---|---|---|
| Polyacrylate-32 | 30.00 | 2.70 |
| Polysilicone-28 | 30.00 | 0.90 |

Total Polymer Activity 3.60
Formula pH Range: 6.00-7.00

The polyacrylate-32 is neutralized using the AMP and the components are mixed together using conventional techniques for formulating a non-aerosol hairspray. Specifically, the composition was made as follows:

1. Add the ingredients individually, mixing at least 5 minutes between each addition: Polyacrylate-32, Aminomethyl Propanol 95%, Polysilicone-28, Bis-PEG-8 Dimethicone.

2. Mix at least 15 minutes, ensuring the batch is clear and uniform before proceeding.

This composition, when applied to the hair using a non-aerosol spray bottle, and low heat is applied to the treated hair using a hair dryer, the hair being styled using a round (cylindrical) styling brush, provides a non-frizzy continuous wave hairstyle, as well as hair which has a natural feel even after being treated.

Additional examples of compositions of the present invention, made using conventional mixing methods are set forth in the following table:

|  | Example 2 Leave-on Cream | Example 3 Smoothing Spray | Example 4 Styling Gel | Example 5 Heat Tool Styling Lotion | Example 6 Hi Hold Style Spray |
|---|---|---|---|---|---|
| Ingredients |  |  |  |  |  |
| Polysilicone-28 | 3.00 | 3.00 | 6.00 | 6.00 | 6.00 |
| Polyacrylate-32 | 3.00 | 9.00 | 18.00 | 18.00 | 27.00 |
| Bis-PEG-8 Dimethicone | 1.00 | 1.00 | 2.00 | 2.00 | 2.00 |
| Hydroxyethylcellulose | 0.00 | 0.00 | 0.75 | 0.75 | 0.00 |
| Cetearyl Alcohol | 4.00 | 0.00 | 0.00 | 0.75 | 0.00 |
| Aminomethyl Propanol | 0.75 | 0.75 | 0.75 | 1.50 | 1.50 |
| Ethanol | 0.00 | 5.00 | 0.00 | 0.00 | 0.00 |
| Fragrances | 0.10 | 0.10 | 0.10 | 0.10 | 0.10 |
| Preservatives | 0.14 | 0.14 | 0.14 | 0.14 | 0.14 |
| Water | 88.01 | 88.01 | 72.26 | 70.76 | 63.26 |
| Total | 100.00 | 100.00 | 100.00 | 100.00 | 100.00 |
| Ratios |  |  |  |  |  |
| % Activity |  |  |  |  |  |
| Polysilicone-28 | 0.90 | 0.90 | 1.80 | 1.80 | 1.80 |
| Polyacrylate-32 | 0.90 | 2.70 | 5.40 | 5.40 | 8.10 |
| Bis-PEG-8 Dimethicone | 1.00 | 1.00 | 2.00 | 2.00 | 2.00 |
| PS-28:PA-32:Silicone | 1:1:1 | 1:3:1 | 1:3:1 | 1:3:1 | 1:4:1 |
| Film Property | Softer Elastic |  | Ideal - Strong and Elastic |  | Harder Less Elastic |

The film characteristics of a composition of the present invention (as shown in Formulational Example 1, above) was evaluated and compared to other similar compositions to better understand the film properties under usage conditions. Several sensory and microscopic evaluations were made of the neat films. The films were prepared by drawing the materials into a film and letting them sit (and cure) over a two-hour period at 80° C. Each of the films had a roughly equal thickness of less than about 0.25 mm. The films were prepared and evaluated under ambient conditions (22-26° C./45-55% RH). Fixed weights were used to determine the force required to break each film. Among the films that were evaluated were the formulation shown in Example 1 (Proto-2065), a film made from a conventional styling copolymer (VP/VA), and films made from commercial products Three Days Straight (3DS) and Go Curlier.

Figure 1:
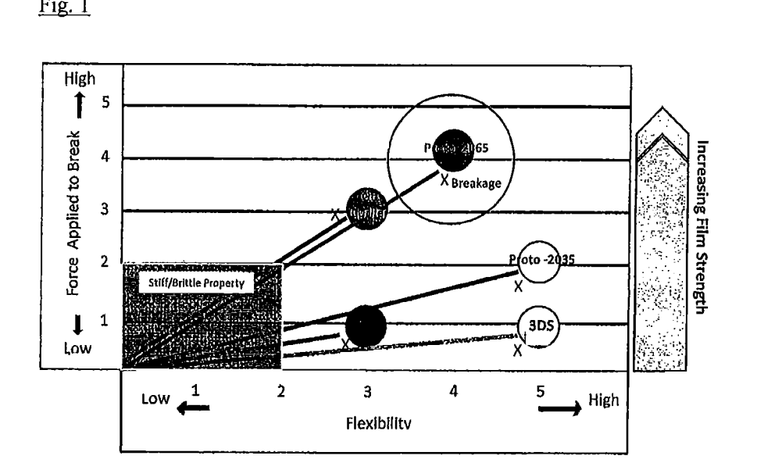
FIG. 1 shows the flexibility and breakage force results of formulational examples 1-6.

The graph labeled FIG. 1 shows the flexibility and the amount of force needed to break each of the films. As can be seen from the graph, the film of the present invention exhibits high tensile strength and flexibility and durability, while conventional polymers are less durable, less flexible and are easier to break.

A microscopic analysis of each of the films was also carried out as follows: The films were created and placed under the microscope for visual surface analysis. A Keyence Digital Microscope was used.

Figure 2:
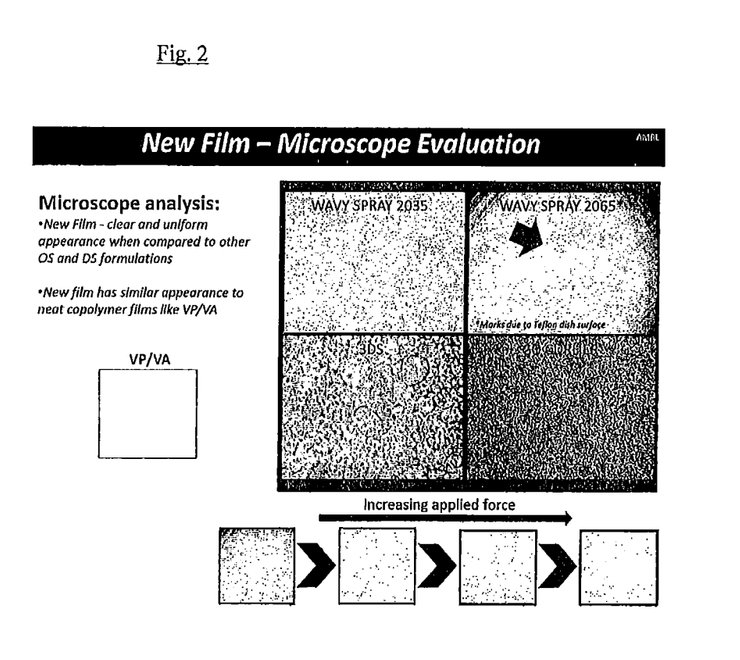
FIG. 2 shows the microscopic analysis of the films of formulational examples 1-6.

The results of this microscopic analysis is shown in FIG. 2:

The film of the present invention is clear and uniform in appearance when compared to the other prior art films. The new film has a similar appearance to neat copolymer films like VP/VA, while exhibiting superior styling properties as described herein.

What is claimed is:

1. A hairstyling composition comprising the following polymers in a hair care vehicle selected from water, alcohol, silicones, oils, hydrocarbons, esters, and combinations thereof:

(a) from about 0.1% by weight to about 5% by weight of polysilicone-28; and
(b) from about 0.3% by weight to about 15% by weight of polyacrylate-32; and
(c) from about 0.1% by weight to about 5% by weight of bis-PEG-8-dimethicone;
wherein the weight ratio (a):(b) is from about 4:1 to about 1:4; and the weight ratio (b):(c) is from about 1:4 to about 4:1.

2. The hairstyling composition according to claim 1 wherein the weight ratio (a):(b) is from about 3:1 to about 1:3 and the weight ratio (b):(c) is from about 1:3 to about 3:1.

3. The hairstyling composition according to claim 1 wherein the weight ratio (a):(b):(c) is from about 1:1:1 to about 1:4:1.

4. The hairstyling composition according to claim 1 wherein the weight ratio (a):(b):(c) is about 1:3:1.

5. The hairstyling composition according to claim 1 formulated as a product selected from shampoos, conditioners, aerosol sprays, non-aerosol sprays, gels and emulsions.

6. The hairstyling composition according to claim 1 formulated as a non-aerosol spray.

7. A method for providing gentle wave frizz-free hair styles comprising the following steps: (a) wetting the hair of a subject; (b) towel-drying the hair; (c) applying to the wet hair from step (b) the composition of claim 1; and (d) applying low heat and high force brushing to the treated hair in order to achieve the desired hairstyle.

8. The method according to claim 7 wherein, in step (c), from about 0.5 to about 8 grams of the composition is applied.

9. The method according to claim 7 wherein the heat is applied by a blow dryer having a temperature of from about 60° C. to about 80° C., and the brushing is accomplished using a round styling brush.

10. The hairstyling method according to claim 7 wherein the composition applied in step (c) is in the form of a non-aerosol spray.

11. The hairstyling method according to claim 7 wherein step (a) includes applying shampoo and/or conditioner to the hair.

\* \* \* \* \*